Figure 1A:
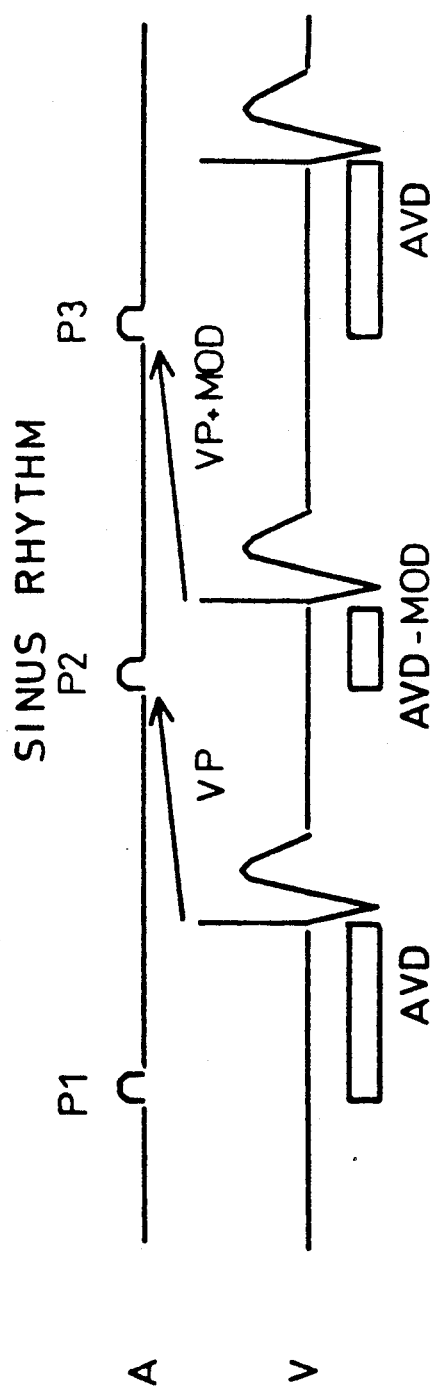

United States Patent [19]
Limousin et al.

[11] Patent Number: 5,167,224
[45] Date of Patent: Dec. 1, 1992

[54] METHOD FOR DETECTING AND CONTROLLING ENDLESS LOOP TACHYCARDIAS OF A HEART BEING CONTROLLED BY A CARDIAC PULSE GENERATOR

[75] Inventors: Marcel Limousin, Montrouge; Rémi Nitsche, Beynes, both of France

[73] Assignee: Ela Medical, Montrouge, France

[21] Appl. No.: 624,105

[22] Filed: Dec. 7, 1990

[30] Foreign Application Priority Data

Oct. 24, 1990 [FR] France .................... 90 13199

[51] Int. Cl.⁵ .......................................... A61N 1/362
[52] U.S. Cl. ........................................ 128/419 PG
[58] Field of Search ............................ 128/419 PG

[56] References Cited

U.S. PATENT DOCUMENTS

| 4,569,350 | 2/1991 | Mumford et al. | 128/697 |
| 4,686,989 | 8/1987 | Smith et al. | 128/419 PG |
| 4,860,749 | 8/1989 | Lehmann | 128/419 PG |

FOREIGN PATENT DOCUMENTS

0118780 9/1984 European Pat. Off. .
2544988 4/1983 France .

Primary Examiner—William E. Kamm
Assistant Examiner—Scott M. Getzow
Attorney, Agent, or Firm—Davis Hoxie Faithfull & Hapgood

[57] ABSTRACT

A method for detecting and controllig endless loop tachycardia (ELT) of a heart being controlled by a cardiac pulse generator.

A measurement is made of the VP time interval over eight cycles and of its maximum deviation which is compared with two threshold values.

A modulation is applied to the atrio-ventricular delay and the following VP time interval is measured during the ninth cycle. The variation of the VP time interval is compared with the threshold values for determining whether one is dealing with an ELT or with a sinus rhythm.

30 Claims, 3 Drawing Sheets

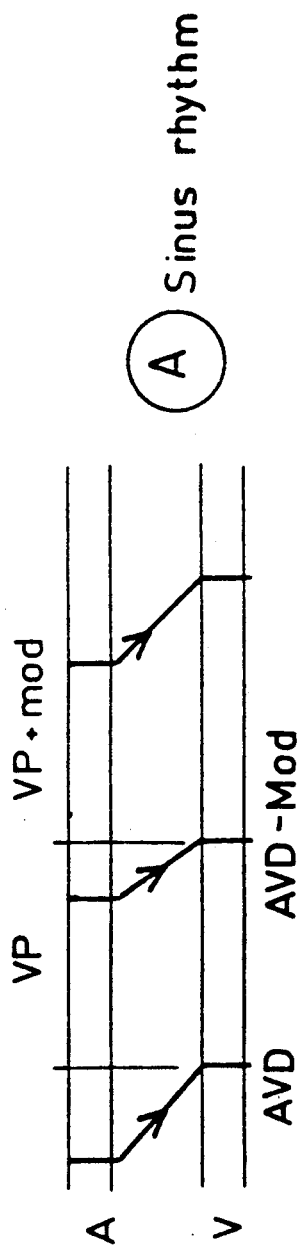
FIG.2a Ⓐ Sinus rhythm
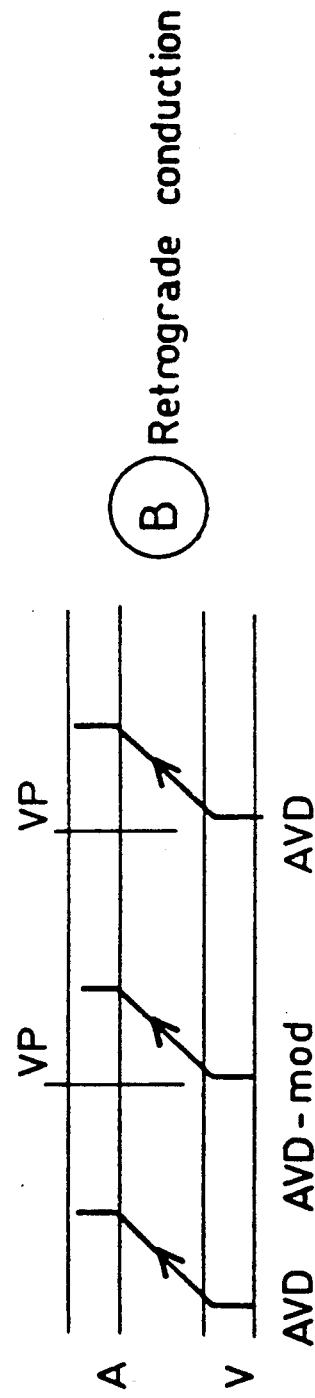
FIG.2b Ⓑ Retrograde conduction
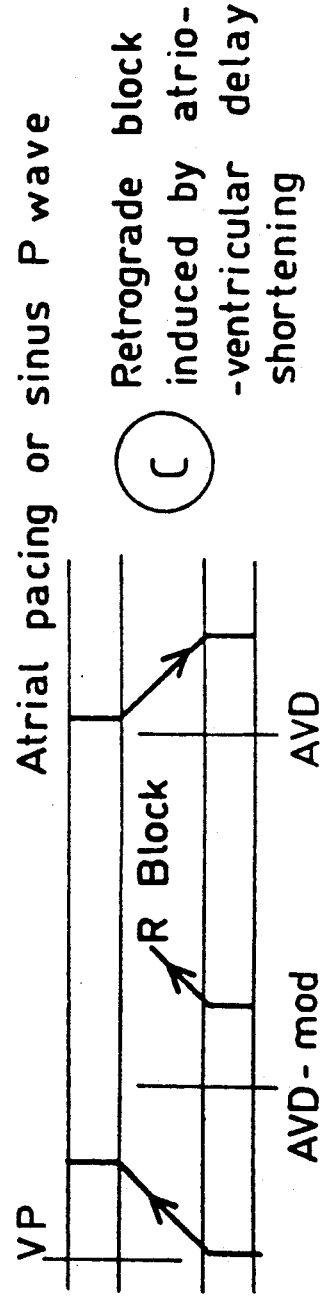
FIG.2c Ⓒ Retrograde block induced by atrio-ventricular delay shortening
Atrial pacing or sinus P wave

METHOD FOR DETECTING AND CONTROLLING ENDLESS LOOP TACHYCARDIAS OF A HEART BEING CONTROLLED BY A CARDIAC PULSE GENERATOR

The present invention relates generally to cardiac pulse generators or pacemakers of the dual-chamber type.

Such pulse generators are adapted for being capable of stimulating the heart atrium and/or ventricule when depolarizations do not occur in a physiological manner.

The normal functioning of a heart causes a contraction of the ventricle to be driven by a contraction of the atrium, this being ascertained by what is called the P wave by cardiologists.

In some cases, the heart presents a retrograde conduction which propagates towards the atrium the wave resulting from the depolarization of the ventricle and causes the depolarization of said atrium. The pulse generator detects this depolarization and interprets it as a usual P wave.

At the end of the atrio-ventricular delay (AVD) the pacemaker will then pace the ventricle in response to this wave. The new depolarization of the ventricle might again generate a retrograde wave which is also misinterpreted and leads to pacing of the ventricle.

The initiating of such a cycle of functioning is extremely hazardous since on the one hand it may occur that the ventricle will be paced at a too rapid rate and, on the other hand, the said ventricle is contracted while it has not been completely filled with blood, which leads to an insufficient cardiac output.

Such a pathology is called endless loop tachycardia (ELT) and it is essential to terminate this tachycardia.

For this, there is the need to differentiate at first whether the acceleration being detected in the heart rythm is due to a sinus tachycardia or else to such an ELT.

One means of differentiation known from document FR-2 544 988 consists in reducing the AVD elapsing between the detection of the P wave and pacing of the ventricle in response to this wave, and then measuring the time interval (called VP) between said pacing of the ventricle and the next P wave.

When dealing with a sinus tachycardia, the acceleration of the cardiac rythm is solely due to the atrium, the rate of which increases.

The interval between two P waves always remains the same, therefore if the AVD is shortened, the VP time interval increases (FIG. 1a).

Figure 1B:
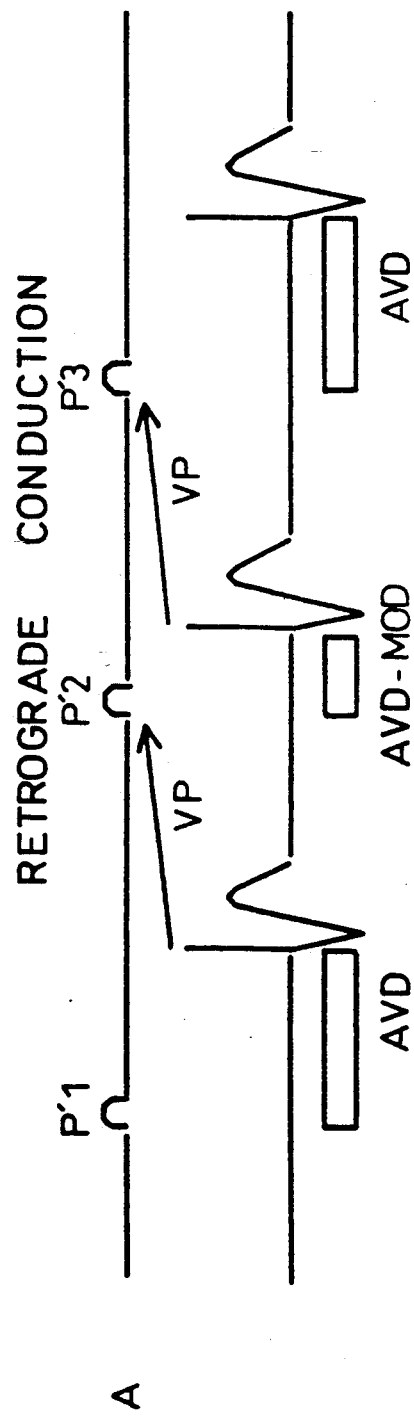

On the contrary, when the acceleration is due to an ELT the ventricle is controlling the atrium, and whatever the AVD maya be, the VP time interval remains stable (FIG. 1b).

This means of differentiation is already being used in cardiac pulse generators in accordance with the FR-2 544 988 document, but always within control procedures which are sometimes too lengthy for the patient, since they risk sustaining the ELT during too much time.

The present invention is therefore related to a new method for controlling ELT occurrences which makes it possible to detect them more promptly, and thus to terminate them at a much earlier time.

Since ELT occurrences are due to dysfunctions or inadequations of the pulse generator's program to the heart condition, the method according to the invention is also aimed at reprogramming the pulse generator quickly in order to avoid a too frequency repetition of such ELT occurrences.

The present invention has for its object a method for detecting and controlling endless loop tachycardias of a heart provided with a heart pulse generator, wherein the risk of an ELT becoming established is appreciated through the fact that the VP time interval between the ventricle pacing and the detection of a P wave is shorter than a value comprised between 400 and 500 milliseconds (ms) and preferably less than 450 ms, characterized in that:

when the VP interval is less than 450 ms, a measurement is made of this interval over a number of heart cycles comprised between 2 and 16, and preferably equal to 8, a calculation is made of the difference between the smallest and the largest of the values of the VP time interval, this difference is compared with a first threshold value, the risk of an ELT being excluded if the said difference is larger than the said first threshold value, in case the said difference is less than the first threshold value, it is compared to a second threshold value which is smaller than the first threshold value, in case the said difference is less than the second threshold value, the AVD is modulated with a first duration and the following VP time interval is measured, if the VP time interval has varied relatively to the preceding ones by a quantity less than the said second threshold value, this means that an ELT is occurring, and the ELT has to be terminated, if the VP time interval has varied relatively to the preceding ones by a quantity comprised between said first and second threshold values,, the AVD is then modulated with a second duration being longer than said first duration, and the VP time interval is measured, if the VP time interval has varied relatively to the preceding ones by a quantity less than said first threshold value, this means that an ELT is occurring, and the ELT has to be terminated.

if the VP time interval has varied by a quantity larger than said first threshold value, this means that no ELT is present, and in case the said difference is larger than the said second threshold value, the AVD is modulated with the said second duration, and one proceeds in the same manner as previously.

According to further features of the invention:

the first threshold value is included within 25 and 40 ms and preferably equal to 31 ms, the second threshold value is included within 10 and 25 ms and preferably equal to 16 ms, the first duration of modulation of the AVD is included between 40 and 55 ms and preferably equal to 47 ms, the second duration of modulation of the AVD is included between 55 and 70 ms and preferably equal to 63 ms, when the VP time interval between the ventricular pacing and detection of a P wave is less than 450 ms, measurements are made of the VP time intervals in a number of consecutive cardiac cycles comprised between 2 and 16, preferably equal to 8, and a calculation is made of the difference between the longest one and the shortest one of these VP time intervals, and this difference is compared with a threshold value which preferably equals 31 ms, when the said calculated difference is more than 31 ms, it is determined that there is no ELT, when the said calculated difference is less than 31 ms, therefore when VP is said to be stable, the said difference is compared with 16 ms, when the said calculated difference is less than 16 ms, the AVD is modulated at 47 ms over one cycle and then, if VP remains stable at 16 ms, it is determined that an ELT is present, and this ELT is terminated, whereas if VP is not stable, the AVD is modulated at 63 ms over one cardiac cycle, when the said calculated difference is more than 16 ms, the AVD is modulated at 63 ms over one cardiac cycle, after modulating at 63 ms, if VP is stable at 31 ms, it is determined that an ELT is present, and this ELT has to be terminated, whereas if VP is not stable, it is determined that there is a sinus tachycardia, when it has been determined that there was a sinus tachycardia, a counter is started in order that the control process will not be resumed before a number of cardiac cycles comprised between 50 and 150, preferably equal to 100, the modulation of the AVD is negative, or else positive when the negative modulation implies either a ventricular pacing rate higher than the programmed upper rate, or a too short AVD, an account is kept, as ELT, of every confirmation of the stability of the VP time interval, as well as of the detection of a retrograde block, the detection of a retrograde block is ascertained when the VP time interval during the tenth cycle after AVD shortening is longer than a (VP max+ | |Mod| | +Ds) value, when there has been recorded a predetermined number, that is of the order of 5, of ELT during one day, a reprogramming of the cardiac pulse generator is initialized.

Figure 3:
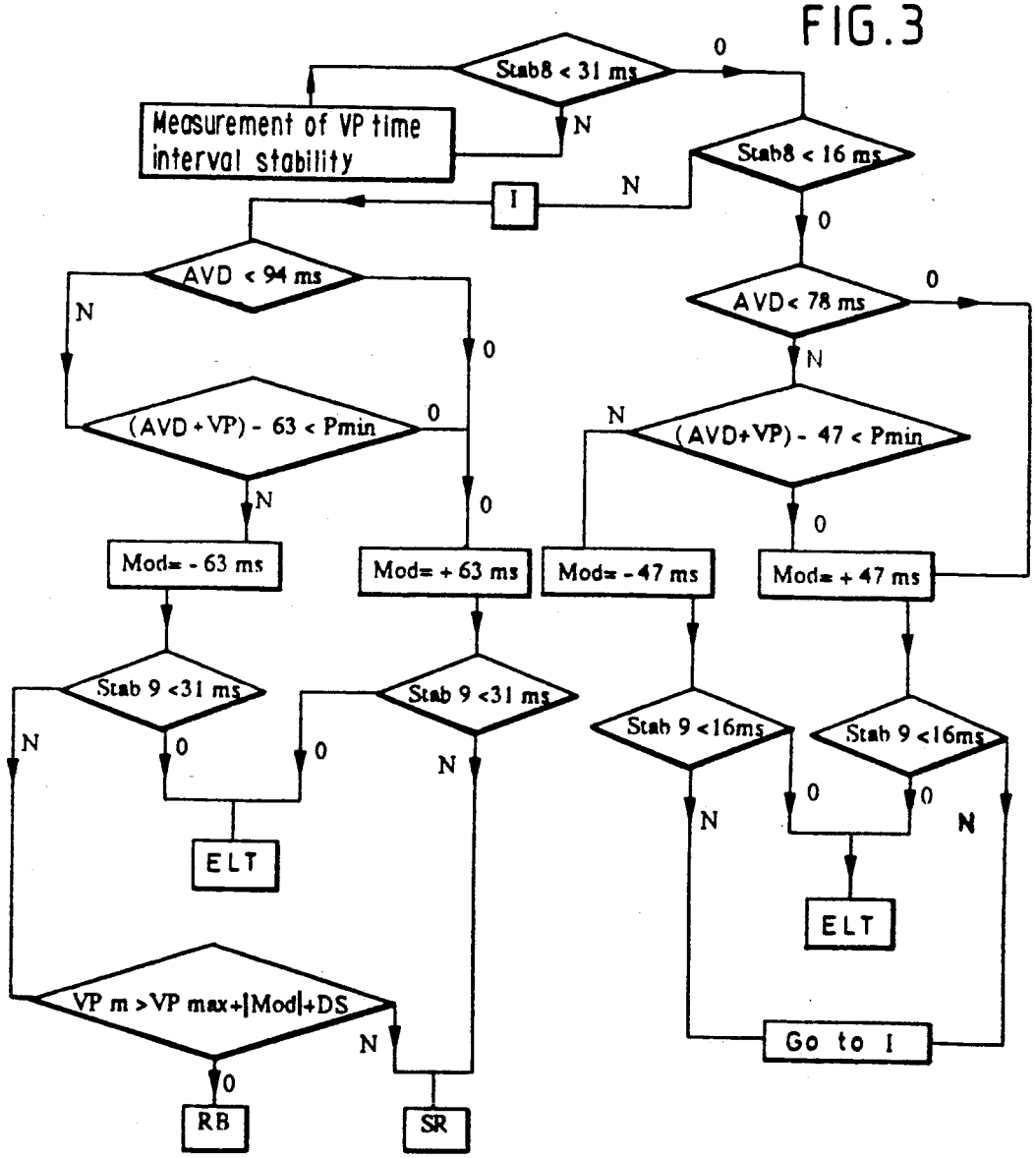

For a better and more explicit description of the invention, there are represented in the appended drawings:

FIG. 1a: a diagrammatic representation of the recordings of the atrium (A) and ventricle (V) in the case of a sinus cardiac rhythm, FIG. 1b: a diagrammatic representation of the same recordings in the case of a retrograde conduction corresponding to an ELT, FIG. 2a: a diagrammatic representation of the cardiac pacing in the case of a sinus rhythm, FIG. 2b: a diagrammatic representation of the cardiac pacing in the case of a retrograde conduction corresponding to an ELT, FIG. 2c: a diagrammatic representation of the cardiac pacing in the case of the appearance of a retrograde block being induced by a ventricular pacing, after an AVD, FIG. 3: a block of the various steps corresponding to the method according to this invention for detecting and controlling the ELT occurrences, in the case of a detection phase of 8 cycles.

It is known that an ELT cannot occur, either when the atrium is paced by the cardiac pulse generator, or else when the ventricle contracts itself spontaneously, or again when the cardiac rhythm is slow. Therefore, the process will not be initialized when one of these conditions is met.

It is also known that when the VP time interval is longer than 450 ms, the following P wave is not a retrograde one, When the VP time interval becomes less than 400 to 500 ms and preferably less than 450 ms, it will be considered that there is a risk of ELT.

In order to control the VP time interval, the method according to this invention consists in monitoring a number of consecutive cycles comprised between 2 and 16 and preferably equal to 8.

During these cycles, the VP time intervals are measured and a calculation is made of the difference between the longest one (VP max) and the shortest one (VP min) of these intervals.

In case this difference is more than 25-40 ms, and preferably more than 31 ms, it can be said that VP is not stable, and therefore that we are not dealing with an ELT but with a sinus tachycardia, therefore a physiological one.

On the contrary, if it is found that VP is stable according to the 31 ms criterion, meaning that the difference between the longest value and the shortest value is less than or equal to 25-40 ms, and preferably less than or equal to 31 ms, then there is a risk of ELT.

The method according to the invention will then distinguish between two cases:

the difference between the VP intervals is less than 31 ms, it is also less than 10-25 ms and preferably less than 16 ms;

the difference between the VP intervals is included within 31 and 16 ms.

In the first case, one modulates over a cardiac cycle at 40-55 ms and preferably at 47 ms, that is one reduces or increases the AVD by 47 ms and VP is observed comparatively with the latest VP intervals having been measured. The modulation is positive if the negative modulation leads to exceeding the programmed upper rate, or if it leads to an AVD which is too short (<31 ms) or negative.

If VP is stable, meaning that it has varied by less than 16 ms, then one is certain of being in presence of an ELT which has to be terminated in a manner which is known per se (ELT box on right hand side, FIG. 3).

If VP is not stable, meaning that it has varied by more than 16 ms, then one cycle (the ninth one) is modulated at 55-70 ms and preferably at 63 ms, and an observation is made of the stability, relatively to 31 ms.

When VP is not stable (box SR, FIG. 3) a counter is started in order not to reactivate the process before a number of cardiac cycles comprised between 50 and 150 and preferably equal to 100, since the tachycardia is from sinus origin and the modulations operated by the process are useless (FIG. 2a).

When VP is stable (ELT box on left hand side, FIG. 3), one is in presence of an ELT to be terminated.

In the second case, that is the one in which the VP difference over eight cycles is comprised between 31 and 16 ms, one modulates AVD on one cycle at 63 ms and one observes the stability relatively to 31 ms.

The conclusions are then the same as hereinabove namely that the tachycardia is sinus if VP is not stable, which triggers the starting up of the counter in order not to reactivate the process before a number of cardiac cycles comprised between 50 and 150 preferably equal to 100, and one is in presence of an ELT if VP is stable.

When the VP time interval after the modulation cycle of the AVD is measured as stable, the tachycardia must be terminated. In the following cycle, an atrial refractory period of 450 ms avoids AVD starting on the next retrograde P wave. At the end of the escape interval, the atrium is paced, and then the ventricle after the AVD: the A-V synchronization is thus reestablished.

The method according to the invention makes it possible, as one may find out, to determine after 10 cardiac cycles whether there is or not an ELT, while the known methods often require some twenty or even more than thirty cardiac cycles for suspecting this ELT.

Another advantage of the method according to the invention resides in its process for counting the ELT occurrences.

Indeed, a record is made as being an ELT of every confirmation of the stability of the VP time, as well as of the appearance of a retrograde conduction block.

This is due to the finding that, in some cases, the reduction of the AVD obtained by increasing the ventricular rate will block the retrograde conduction and will immediately break off the ELT (FIG. 2c) or will slow it down for one cycle.

The ELT occurrences of this type are not identified by the known control methods, which can prove as dangerous for the pulse generator wearer.

The detection and control process according to the invention provides for the detection of retrograde blocks. When, during the ninth cycle in the case of a negative modulation, it has been found that VP is not stable relatively to 31 ms, one compares it to the value (VP max+ |51 Mod | |+Ds) in which VP max is the highest measured value of VP during the eight previous cycles, | |Mod| | is the absolute value of the modulation of the AVD, and Ds is a safety duration included within 50 and 150 ms and preferably equal to 100 ms.

If VP m, the VP time during the tenth cycle, is more than this value, one is in presence of a retrograde block (box RB in FIG. 3) and it is recorded as an ELT in a particular counter.

Each time when this counter has reached a determined number, for instance 5, over one day, the control method according to the invention will initialize a reprogramming of the pulse generator tending to modify the parameters in order to avoid further ELT. Such a counting method ensures that no ELT will be undetected and it allows for a very quick reprogramming of the pulse generator before there is a risk of the situation becoming serious.

The method which is the subject matter of this invention has been described as using reductions of the AVD. Without departing form the scope of the present invention, the said AVD may be increased, since the determination of the ELT throught the stability of VP will then in no way be called again into question.

It should therefore understood that the above mentioned modulations are plus or minus variations.

Negative variations will be preferred whenever possible since they enhance the termination of an ELT.

Positive variations will be applied when the diminution of the AVD would risk brining about a value less than the minimum possible value, or even a negative one, or else when the ventricular pacing rate would risk exceeding the programmed upper rate.

We claim:

1. A method for detecting possible endless loop tachycardias (ELT) of a heart controlled by a cardiac pacemaker that detects atrial depolarization as P wave and paces the ventricle after a selected atrio-ventricular delay (AVD) following a P wave comprising:
   (A) monitoring the VP time interval between the ventricle pacing and a following P wave;
   (B) comparing the VP time interval to a time value selected from between 400 and 500 msec; and
   (C) determining that there is minimal risk of an ELT if the VP interval is greater than the time value and determining that there is risk of an ELT if the VP interval is less than the time value, wherein step (C) further comprises:
   (D) monitoring the VP interval for each of plurality of cardiac cycles in response to a determination of risk of ELT;
   (E) calculating the difference VP between the maximum and minimum VP intervals of the plurality of cardiac cycles;
   (F) comparing the calculated VP to a first threshold; and
   (G) determining that there is minimal risk of ELT if the calculated VP is greater than the first threshold and determining that there is a risk of ELT if the calculated VP is less than the first threshold.

2. The method of claim 1 wherein step (G) further comprises comparing the calculated $\Delta$VP to a second threshold in response to the calculated $\Delta$VP being less than the first threshold and further processing the difference VP intervals according to step (I) if the calculated $\Delta$VP is below the second threshold and according to step (H) if the calculated $\Delta$VP is not below the second threshold, wherein
   step (H) comprises:
   (i) modulating the AVD by a first duration;
   (ii) determining the VP interval using the modulated AVD for one cardiac cycle following the plurality of cardiac cycles;
   (iii) calculating a second difference $\Delta$VP2 between the maximum and minimum VP intervals of the plurality of cardiac cycles and the one following cardiac cycle; and
   (iv) determining that there is ELT if the calculated $\Delta$VP2 is less than the first threshold and that there is no ELT if the calculated $\Delta$VP2 is not less than the first threshold; and
   step (I) comprises:
   (i) modulating the AVD by a second duration;
   (ii) determining the VP interval using the modulated AVD for a first one cardiac cycle following the plurality of cardiac cycles;
   (iii) calculating a third difference $\Delta$VP3 between the maximum and minimum VP intervals of the plurality of cardiac cycles and the first one following cardiac cycle;
   (iv) determining that there is ELT if the calculated $\Delta$VP3 is less than 16 msec and, if $\Delta$VP3 is not less than 16 msec:
     (1) modulating the AVD by the first duration;
     (2) determining the VP interval using the modulated AVD for a second one cardiac cycle following the plurality of the cardiac cycles and the first one cardiac cycle;
     (3) calculating a fourth difference $\Delta$VP4 between the maximum and minimum VP intervals of the plurality of cardiac cycles and the second one following cardiac cycle; and
     (4) determining that there is ELT if the calculated $\Delta$VP4 is less than the first threshold and that there is no ELT if the calculated $\Delta$VP4 is not less than the first threshold.

3. The method of claim 2 wherein the first threshold is selected from between 25 and 41 ms.

4. The method of claim 2 wherein the second threshold is selected from between 10 and 25 ms.

5. The method of claim 2 wherein the first duration of modulation of the AVD is selected from between 40 and 55 ms.

6. The method of claim 2 wherein the second duration of modulation of the AVD is selected from between 55 and 70 ms.

7. The method of claim 2 wherein the plurality of cardiac cycles is selected from between 2 and 16 cycles.

8. The method of claim 2 wherein the time value is less than 450 ms, the first threshold is on the order of 31 ms, the second threshold is on the order of 16 ms, the first duration of modulation is on the order of 47 ms, the second duration is on the order of 63 ms, and the plurality of cardiac cycles is on the order of 8.

9. The method of claim 2 further comprising recording as an ELT event every confirmation of the stability of the VP interval and every detection of a retrograde block.

10. The method of claim 9 wherein the detection of a retrograde block comprises determining when the VP interval during the second one cardiac cycle exceeds a value corresponding to the sum of the maximum VP interval MOD and a safety duration, wherein MOD is the absolute value of the modulation of the AVD and the safety duration is selected from between 50 and 150 ms.

11. The method of claim 9 further comprising reprogramming the pacemaker in response to the occurrence of more than a selected number of ELT events during a selected time period.

12. The method of claim 11 wherein the selected number is on the order of 5 and the selected time period is on the order of a day.

13. A method for detecting possible endless loop tachycardia events of a heart controlled by a pacemaker that detects atrial depolarizations as P waves and paces the ventricle after a selected atrio-ventricular delay (AVD) following a P wave, comprising:
determining a first VP time interval between the ventricle pacing and a following P wave;
determining the VP intervals during a plurality of cardiac cycles selected from between 2 and 16 cycles, in response to the first VP time interval being less than 450 ms;
calculating the difference $\Delta$VP between the longest and shortest of the determined VP intervals for the plurality of cardiac cycles; and
comparing the calculated $\Delta$VP to a first threshold period on the order of 31 ms.

14. The method of claim 13 further comprising determining that there is no endless loop tachycardia if the calculated $\Delta$VP is greater than the first threshold period.

15. The method of claim 13 further comprising:
determining that the VP time interval is stable if the calculated $\Delta$VP is less than the first threshold; and
comparing the calculated $\Delta$VP to a second threshold period on the order of 16 ms.

16. The method of claim 15 further comprising:
modulating the AVD by a first amount on the order of 47 ms over one cardiac cycle in response to the calculated $\Delta$VP being less than the second threshold period;
determining that there is an endless loop tachycardia to be terminated if the VP time interval is stable at the second threshold period; and
modulating the AVD by a second amount on the order of 63 ms over one cardiac cycle if the VP time interval is not stable at the second period.

17. The method of claim 16 further comprising:
determining whether the VP time interval is stable at a third threshold on the order of 31 ms after modulation by the second amount;
determining that an endless loop tachycardia is present if the VP time interval is stable at the third threshold period; and
determining that there is a sinus tachycardia if the VP time interval is not stable at the third threshold period.

18. The method of claim 7 further comprising counting the number of cardiac cycles following the determination of a sinus tachycardia and resuming the control process after the occurrence of a number of cardiac cycles selected from between 50 and 100 cardiac cycles.

19. The method of claim 15 further comprising modulating the AVD by a first amount on the order of 63 ms in response to the calculated $\Delta$VP being greater than the second threshold.

20. The method of claim 19 wherein the modulation of the AVD is one of negative and positive, the positive modulation occurring when a negative modulation implies one of a ventricular pacing rate higher than a programmed pacing rate and an AVD that is shorter than a selected minimum AVD.

21. The method of claim 16 wherein the modulation of the AVD is one of negative and positive, the positive modulation occurring when a negative modulation implies one of a ventricular pacing rate higher than a programmed pacing rate and an AVD that is shorter than a selected minimum AVD.

22. Apparatus for detecting possible endless loop tachycardias (ELT) of a heart controlled by a cardiac pacemaker that detects atrial depolarization as a P wave and paces the ventricle after a selected atrio-ventricular delay (AVD) following a P wave comprising:
means for calculating the VP time interval between each ventricle pacing and a following P wave;
first means for comparing a calculated VP time interval to a time value selected from between 400 and 500 msec;
first means for determining that there is minimal risk of an ELT if the calculated VP interval is greater than the selected time value and that there is risk of an ELT if the calculated VP interval is less than the selected time value;
means for calculating the difference VP between the maximum and minimum calculated VP intervals during a plurality of cardiac cycles selected from between 2 and 16 cycles in response to a determination of risk of ELT;
second means for comparing the calculated VP to a first threshold selected from between 25 and 41 ms; and
second means for determining that there is no ELT if the calculated VP is greater than the first threshold and that there is risk of ELT if the calculated VP is less than the first threshold.

23. The apparatus of claim 22 further comprising:

third means for comparing the calculated $\Delta VP$ to a second threshold selected from between 10 and 25 ms in response to the calculated $\Delta VP$ being less than the first threshold:

a first means, responsive to the calculated $\Delta VP$ being not below the second threshold, for further processing the calculated VP intervals comprising:

first means for modulating the AVD by a first duration selected from between 55 and 70 ms for a first one cardiac cycle following the plurality of cardiac cycles;

third means for calculating a second difference $\Delta VP2$ between the maximum and minimum calculated VP intervals of the plurality of cardiac cycles and the first one following cardiac cycle; and third means for determining that there is ELT if the calculated $\Delta VP2$ is less than the first threshold and that there is no ELT if the calculated $\Delta VP$ is not less than the first threshold; and a second means, responsive to the calculated $\Delta VP$ being below the second threshold, for processing the calculated VP intervals comprising:

second means for modulating the AVD by a second duration selected from between 40 and 55 ms for a second one cardiac cycle following the plurality of cardiac cycles;

fourth means for calculating a third difference $\Delta VP3$ between the maximum and minimum VP intervals of the plurality of cardiac cycles and the second one following cardiac cycle;

four means for determining that there is ELT if the calculated $\Delta VP3$ is less than 16 msec; and third processing means, responsive to the calculated $\Delta VP3$ being not less than 16 msec, for processing the calculated VP intervals, further comprising:

third means for modulating the AVD by the first duration for a third one cardiac cycle following the plurality of the cardiac cycles;

fifth means for calculating a fourth difference $\Delta VP4$ between the maximum and minimum VP intervals of the plurality of cardiac cycles and the third one following cardiac cycle; and fifth means for determining that there is ELT if the calculated $\Delta VP4$ is less than the first threshold and that there is no ELT if the calculated $\Delta VP4$ is not less than the first threshold.

24. The apparatus of claim 23 wherein the selected time value is less than 450 msec, the first threshold is on the order of 31 ms, the second threshold is on the order of 16 ms, the first duration is on the order of 47 ms, the second duration is on the order of 63 ms, and the plurality of cardiac cycles is on the order of 8.

25. The apparatus of claim 23 further comprising means for recording as an ELT event every confirmation of the stability of the calculated difference VP intervals and every detection of a retrograde block.

26. The apparatus of claim 25 wherein a retrograde block is recorded when the VP interval during the third following cardiac cycle exceeds a value corresponding to the sum of the maximum VP interval MOD and a safety duration, wherein MOD is the absolute value of the modulation of the AVD and the safety duration is selected from between 50 and 150 ms.

27. The apparatus of claim 25 further comprising means for reprogramming the pacemaker in response to the occurrence of more than a selected number of ELT events during a selected time period.

28. The apparatus of claim 27 wherein the selected number is on the order of 5 and the selected tim period is on the order of a day.

29. The apparatus of claim 23 further comprising:

sixth means for determining that there is a sinus tachycardia if the calculated $\Delta VP3$ is not less than the third threshold period; and means for counting the number of cardiac cycles following a determined sinus tachycardia and resuming the control process after the occurrence of a number of cardiac cycles selected from between 50 and 100 cardiac cycles.

30. The apparatus of claim 23 wherein the modulation of the AVD is one of negative and positive, the positive modulation occurring when a negative modulation implies one of a ventricular pacing rate higher than a programmed pacing rate and an AVD that is shorter than a selected minimum AVD.

* * * * *

UNITED STATES PATENT AND TRADEMARK OFFICE
CERTIFICATE OF CORRECTION

PATENT NO. : 5,167,224

DATED : December 1, 1992

INVENTOR(S) : Limousin et al

It is certified that error appears in the above-indentified patent and that said Letters Patent is hereby corrected as shown below:

Title page, references cited, "2544988 4/1983 FRANCE" should be --2544988 11/1984 France--.

Column 1, line 54, "maya be" should be "may be".

Column 2, line 38, after "values" delete ",".

Column 2, line 45, after "terminated" delete "." and insert --,--.

Column 3, line 64, after "8" insert --cardiac--.

Column 5, line 32, "|51" should be --||--.

Column 5, line 56, after "therefore" insert --be--.

Column 5, line 68, after "as" insert --a--.

Column 8, line 19, "7" should be "17".

Column 8, line 50, "msec" should be "ms".

UNITED STATES PATENT AND TRADEMARK OFFICE
CERTIFICATE OF CORRECTION

PATENT NO. : 5,167,224
DATED : December 1, 1992
INVENTOR(S) : Limousin et al

It is certified that error appears in the above-indentified patent and that said Letters Patent is hereby corrected as shown below:

Column 9, line 19, "$\Delta VP$" should be --$\Delta VP2$--.

Column 9, line 32, "four" should be --fourth--.

Column 10, line 28, "tim" should be --time--.

Signed and Sealed this

Twenty-seventh Day of December, 1994

Attest:

BRUCE LEHMAN

Attesting Officer          Commissioner of Patents and Trademarks